United States Patent [19]

Kojima et al.

[11] 4,075,334

[45] Feb. 21, 1978

[54] 6β-IODOMETHYL-19-NORCHOLEST-5(10)-EN-3β-OL AND COMPOSITIONS CONTAINING SAME

[75] Inventors: Masaharu Kojima, Fukuoka; Hiroshi Ogawa, Chiba; Minoru Maeda, Fukuoka; Kazuo Nitta; Takayuki Ito, both of Chiba, all of Japan

[73] Assignee: Mallinckrodt, Inc., St. Louis, Mo.

[21] Appl. No.: 562,666

[22] Filed: Mar. 27, 1975

[30] Foreign Application Priority Data

May 20, 1974 Japan .................................. 49-56822

[51] Int. Cl.$^2$ .......................... C07J 9/00; A61K 31/56
[52] U.S. Cl. .................................. 424/238; 260/397.2
[58] Field of Search ...................................... 260/397.2

[56] References Cited

U.S. PATENT DOCUMENTS 3,784,576   1/1974   Counsell ........................... 260/397.2

OTHER PUBLICATIONS

"Steroids" by Counsell, vol. 16 (1970) pp. 317–328.
Journal of the Chemical Soc. Chemical Comm. (Jan. 1975) No. 2, p. 47 relied on.
Journal of Nuclear Medicine 16, No. 6, June 1975, pp. 514, 542 and 565.

Primary Examiner—Elbert L. Roberts
Attorney, Agent, or Firm—Roy J. Klostermann

[57] ABSTRACT

Iodinated compounds useful for photoscanning the adrenal glands.

10 Claims, No Drawings

6β-IODOMETHYL-19-NORCHOLEST-5(10)-EN-3β-OL AND COMPOSITIONS CONTAINING SAME

FIELD OF THIS INVENTION

This invention relates to 6β-iodomethyl-19-norcholest-5(10)-en-3β-ol, radioiodinated analogs thereof, their preparation and to the use of such analogs as scanning agents for the adrenal gland.

DESCRIPTION OF THE PRIOR ART 19-iodocholesterol and radioiodinated analogs thereof are described in U.S. Pat. No. 3,784,576 and in R. E. Counsell et al, Steroids Vol. 16, 317 – 328, 1970.

BRIEF DESCRIPTION OF THE INVENTION

Briefly, a compound of this invention is represented by the following formula.

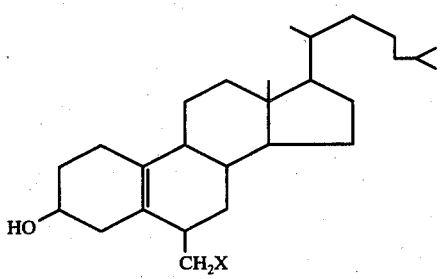

I where X is iodine or radioactive iodine, said compound being substantially free of 19-iodocholest-5-en-3β-ol and radioiodinated-19-iodocholest-5-en-3β-ol.

Another aspect of this invention is directed to a substantially pure compound represented by formula I.

Another aspect of this invention is directed to a composition comprising 80 to 99% by weight, based on the total weight of the composition, of a compound represented by formula I and about 1 to 20% by weight, based on the total weight of the composition, of 19-iodocholest-5-en-3β-ol, radioiodinated-19-iodocholest-5-en-3β-ol, or mixtures thereof.

Another aspect of this invention is directed to the use of the radioactive compounds and compositions as adrenal scanning agents.

Another aspect of this invention is directed to the preparation of a compound represented by formula I which comprises a. heating for a sufficient time and at a sufficient temperature to rearrange the substituent in the 19-position to the 6-position, a composition comprising 1. a compound represented by the formula

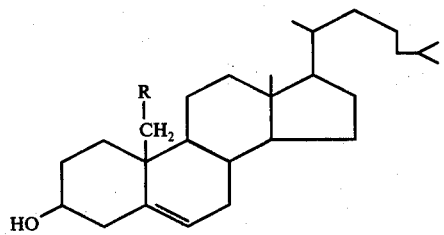

II wherein R is a substituted sulfonyl group or a halogen atom, 2. sufficient iodine, alkali metal iodide, alkali metal radioactive iodide, ammonium iodide, ammonium radioactive iodide or mixtures thereof, and 3. an inert organic solvent; provided, however, when R of such formula is iodine such composition comprises (1) said compound, (2) alkali metal radioactive iodide, or ammonium radioactive iodide, and (3) such solvent or such composition comprises (1) such compounds and (2) such solvent; and further provided when R of such formula is radioactive iodine such composition comprises (1) the compound and (2) the solvent.

b. separating the compound represented by formula I by chromatography.

Surprisingly the radiactive compounds and compositions of this invention give an adrenal gland scan far superior to one obtained using the radioiodinated-19-iodocholest-5-en-3β-ol (hereinafter CL-19-I*). In addition the side of the dosage used can be reduced, and, as a result, the exposure of the patient to radioactive rays can be reduced.

The compounds and compositions of this invention were found while repeating the work of Counsell et al. By following the procedures of Counsell et al mixtures containing about 90% 19-iodocholest-5-en-3β-ol (hereinafter CL-19-I) and 10% 6β-iodomethyl-19-norcholest-5(10)-en-3β-ol (hereinafter NCL-6-I) of this invention were produced. On the other hand, by following the process of the present invention mixtures containing about 90% NCL-6-I and about 10% of CL-19-I were produced from which the compounds of the present invention can be isolated by chromatography.

DETAILED DESCRIPTION OF THE INVENTION

As mentioned, X in formula I can be radioactive iodine. Examples of such isotopes of iodine are $I^{123}$, $I^{124}$, $I^{125}$, $I^{126}$, $I^{127}$ and $I^{131}$; $I^{125}$ and $I^{131}$ are preferred.

Examples of starting materials represented by formula II wherein R is a substituted sulfonyl group that may be used in the practice of the process of this invention include those wherein R is $R^1$-SO$_2$O - wherein $R^1$ is an alkyl group, phenyl, or alkylphenyl with the alkyl group having 1 to 10 carbon atoms preferably 1 to 5 carbon atoms. Specific examples include 19-P-toluenesulfonyloxycholesterol
19-phenylsulfonyloxycholesterol
19-ethylphenylsulfonyloxycholesterol
19-methylsulfonyloxycholesterol
19-amylsulfonyloxycholesterol
19-amylphenylsulfonyloxycholesterol
19-P-toluene-sulfonyloxycholesterol is preferred.

Iodine or radioactive iodine may be used as one of the reactants in the process of this invention. Specific isotopes include $I^{123}$, $I^{124}$, $I^{125}$, $I^{126}$, $I^{127}$ or $I^{131}$. Alkali metal or ammonium salts of iodine or radioactive iodine may also be used. For example, the potassium, sodium or lithium salts.

A sufficient amount of iodine, radioactive iodine or salts thereof is used in the practice of the process of this invention to replace substantially all of the substitutent in the R position with iodine or radioactive iodine. Generally this is an amount that is stoichiometrically required to replace the substituent in the R position. It is preferred that this amount be in slight excess, i.e. about 1 to 10%.

Any inert organic solvent may be utilized in the practice of this invention provided that the solvent does not react nor obstruct substituent transfer to the 6-position. Such solvents include polar solvents such as acetic acid, propanol, isopropanol and acetonitrile. Sufficient solvent is present to solubilize the reactants.

The reactants are generally heated at a sufficient temperature and for a sufficient time to effect rearrangement of the substituent in the 19 position to the 6 position. Generally heating at about 80° C. for a sufficient time ordinarily three hours or longer is desirable. However an excessively long heating time causes decomposition of the product resulting in a decrease in the yield. Usually this time is from 2 to 8 hours. Provided that the heating time is long enough to complete the group transfer to the 6th position, a temperature lower than 80° may be used.

After the rearrangement reaction, the reaction solution is concentrated under reduced pressure, water is added and an extraction with ether is performed. The ethereal extract is washed with water and dried with anhydrous sodium sulfate and the ether is removed by distillation. The product is developed by chromatography. Suitable developing solvents are utilized such as chloroform, butanol, etc. Suitable packing materials such as silica gel, or alumina may be used. Chromatography is well known to those skilled in the art as well as how to use it. In this way substantially pure compounds of this invention are obtained.

In order to radio-label this compound, radioactive iodine in a suitable solvent such as benzene, for example, is concentrated to the dry solid state and labelling occurs on the addition of an unlabelled compound of this invention in acetone. Water is added and the reaction solution is extracted with ether. The extract is washed with sodium thiosulfate solution, water, dried with anhydrous sodium sulfate, and the ether is removed by distillation. In this way radioactive iodine labelled radioiodinated NCL-6-I (hereinafter NCL-6-I*) is obtained. Sufficient radioactive iodine is used to replace substantially all the substituent R. Usually this is about the stoichiometric amount needed to replace the substituent R.

Alternatively, Compound II (R=iodine) can be heated directly to perform the rearrangement, or it may be heated with radioactive iodine, salts thereof or a mixture of the two to perform the rearrangement reaction and labelling at the same time. Also, if R of compound II is a substituted sulfonyl group or a halogen atom other than iodine, it may be heated with radioactive iodine or salts thereof in an amount exceeding the theoretical reacting amount to bring about the thermal rearrangement reaction, the exchange reaction with iodine and the labelling reaction at the same time. Furthermore, as an aspect of this invention CL-19-I* may be used as starting material.

As mentioned the compounds of this invention localize in the adrenal cortex to provide a definitive scan of this organ as its uptake ratio here is greater than in the adrenal per se. Scans of the organ utilizing known techniques would then enable a practitioner to visualize anatomical and functional differences in the adrenal gland, e. g., adrenocortical carcinomas, Cushing's syndrome. The amount of such compound to be utilized in each patient is determined by known procedures as the amount of radioactivity will determine the volume amount to be injected into a patient. A useful amount is one which provides from about 0.1 mCi to 10 mCi per dose with from about 0.5 mCi to about 5 mCi being the preferred range.

The invention will now be illustrated by the following examples.

EXAMPLE 1

200 mg of 19-tosyloxycholesterol and 100 mg of sodium iodide are dissolved in 15 ml of isopropanol and 1.5 ml of water, and they are heated at reflux for 4 hours. Isopropanol is evaporated under reduced pressure, water is added and extraction with ether is performed. After washing the ethereal layer and drying with anhydrous sodium sulfate, the solvent is removed by distillation leaving a residue amounting to 160 mg. The residue is purified by column chromatography (silica gel column about 20 cm in length using chloroform as the developing solvent) and by preparative thin layer chromatography (silica gel developed with chloroform), with fractions corresponding to $R_f = 0.27$ being collected. About 100 mg of pure NCL-6-I is obtained as a glass like solid substance. The structure of this product was confirmed from the results of NMR, IR, and mass spectrography.

Optical Rotation. $[\alpha]_D^{23} = +39°$ (C=1 Cyclohexane)

Elementary analysis values (as $C_{27}H_{45}IO$) C: 63.29; H: 8.95% (theoretical values: C: 63.27; H: 8.85%) m/e 512 ($M^+$)

U.V.: $\lambda_{max}$ cyclohexane 228 nm ($\epsilon$ 7290) and sh 259 nm ($\epsilon$ 3020)

IR: $\nu_{max}$(KBr) 3365 cm/−1 (OH)

NMR: $\delta$(CDCl$_3$)

0.68 (S, 3H, $C_{18}$ methyl)

2.07 (OH, exchanged with heavy water)

3.08 (t, 1H, JIOH$_a$, 6-CH$_2$I) and 3.50 (1H, dd, JIOH$_a$, 2H$_a$, 6-CH$_2$I) (AB part of an ABX system comprising of the methylene and the 6α-hydrogen)

3.97 ppm (1H, m, C$_3$ hydrogen)

Sodium iodide - $^{131}$I (60 millicuries) and a small amount of benzene is solidified by evaporation drying. Acetone (5 ml) and 30 mg of NCL-6-I are added and the solution is heated at reflux for 4 hours. The reaction mixture is diluted with ether and washed with dilute sodium thiosulfate solution and water. The ethereal extract is dried with anhydrous sodium sulfate overnight and the ether is removed to provide about 40 millicuries of NCL-6-I*.

EXAMPLE 2

50 mg of CL-19-I and 25 mg of sodium iodide in 4 ml of isopropanol is reacted and worked up in the same way as described in the first stage of Example 1. About 25 mg of NCL-19-I is obtained.

EXAMPLE 3

100 mg of 19-tosyloxycholesterol and 50 mg of iodine in 8 ml of isopropanol was refluxed with heat for about 3 hours. Then, by the treatment described in Example 1, about 70 mg of NCL-19-I is obtained.

EXAMPLE 4

46 mg of CL-19-I and iodide in a catalystic amount are dissolved in 4 ml of isopropanol, and the solution was refluxed by heating for 7 hours. With the workup described in Example 1, 32 mg of NCL-19-I is obtained.

EXAMPLE 5

50 mg of CL-19-I in 4 ml of isopropanol is refluxed with heat for about 7 hours. Using the workup described in Example 1, 25 mg of NCL-19-I is obtained.

EXAMPLE 6

70 mg of 19-tosyloxycholesterol, 20 mg of sodium iodide and 80 millicurie of sodium iodide -$^{131}$I were added to 15 ml of isopropanol and 1.5 ml of water, and the solution was heated at reflux for 3 hours. The solvent is removed under reduced pressure, water is added, and extraction with ether is carried out. The ethereal layer is washed with water, and is dried with anhydrous sodium sulfate. The solvent is removed by distillation, and the residue is chromatographed on a silica gel column about 20 cm in length using chloroform as the developing solvent to provide about 35 millicurie of pure NCL-6-I*.

EXAMPLE 7

44 mg of CL-19-I in 4 ml of acetic acid is heated at 80° C. for 3.5 hours. After the solution is cooled to room temperature, extraction with ether-water mixed solvent is performed, and, after the separation of the aqueous layer, extraction with ether is performed. The ethereal extract is washed with water, 5% sodium bicarbonate solution, and water in sequence. After drying with anhydrous sodium sulfate, ether is removed by distillation. The residue is purified by silica gel column chromatography. In this way 25 mg of NCL-6-I is obtained.

EXAMPLE 8

2 millicurie of CL-19-I* (I$^{131}$) in 1 ml of isopropanol is treated in the same way as described in Example 5, and 1.4 millicurie of NCL-6-I* is obtained.

EXAMPLE 9

60 millicurie of I$^{131}$ in 5 ml of acetone containing 30 mg of NCL-6-I is heated at reflux for 4 hours. The same labelling treatment as in Example 1 is carried out to produce about 40 millicurie of NCL-6-I*.

EXAMPLE 10

A 30 mg sample of the residue amounting to about 160 mg, which was obtained in a manner similar to that described in the first part of Example 1, is treated in a manner similar to that used in the latter part of Example 1 using 60 mc of Na$^{131}$I to produce a mixture of the NCL-6-I* and CL-19-I*. This mixture was separated by thin layer chromatography on Silica Gel F254 (Merck and Company) (developed with chloroform) to give spots at R$_f$0.27 (NCL-6-I* and R$_f$0.20 (CL-19-I*), and these spots were scraped off and their activities measured to investigate the composition of each component. According to these results, the reaction products comprised 88% NCL-6-I* and 12% CL-19-I*.

EXAMPLE 11

The residue from Example 3 was treated in a manner similar to that used in Example 10 to investigate the composition, and the results obtained showed that the products comprised 84% NCL-6-I and 16% CL-19-I.

EXAMPLE 12

The residue obtained by extraction with ether after the reaction in Example 6 was treated in a manner similar to that of Example 10 to investigate the composition, and the results obtained showed that the product comprised 86% NCL-6-I* compound and 14% Cl-19-I*.

EXAMPLE 13

Using the method of Counsell, 200 mg of 19-tosyloxycholesterol and 100 mg of sodium iodide were refluxed for 4 hours under a steam of nitrogen in 15 ml of isopropanol to prepare CL-19-I, 100 mg of which was refluxed for 4 hours in acetone under an atmosphere of nitrogen with Na$^{131}$I, which was followed by extraction with ether, washing with water and drying to yield a residue. This residue was separated by thin layer chromatography on alumina (chloroform-ethanol 1:1) and the fraction with an R$_f$value of 0.66 was collected. The residue and the purified product were studied to determine their composition in a manner similar to that described in the latter part of Example 10, and the results obtained showed that the crude residue comprised 87% CL-19-I* and 13% NCL-6-I*, while the purified product comprised 89% CL-19-I* and 11% NCL-6-I*.

EXAMPLE 14

CL-19-I*, which has been used as an agent for adrenal gland radiography and NCL-6-I* are compared with respect to the rate of accumulation in the adrenal glands.

20 microcurie (about 20 mcg) each of CL-19-I* (I$^{131}$) and NCL-6-I* (I$^{131}$) were administered to rats ( ♂ ), each about 130 g in weight, through the tail vein. Then several organs were removed after given periods of time to be measured for radioactivity. The accumulation in the adrenal glands expressed as the ratio between the suprarenal glands and liver concentrations measured 6 days after administration is 80 in the case of CL-19-I*, while 840 is observed in the case of NCL-6-I*.

In other words, the adrenal gland/liver ratio for the latter compound is confirmed to be ten times higher than that for the former.

EXAMPLE 15

In a manner similar to that of Control Example 14, radioactive iodine tracer compounds were administered at a dosage of 50μC to male rats of body weight 150g (the weight of the suprarenal is 0.035–0.048g), followed by removal of the suprarenal seven days later later to determine its weight and radioactivity. This give the percentage accumulation in the suprarenal (% dose) which was then divided by the weight of the suprarenal to derive the quantity (% dose/g). The results obtained are presented in the following table.

| Iodine radioisotope labelled compound | % dose/g |
|---|---|
| Purified product from Example 10 NCL-6-I* | 136.6 |
| Product mixture obtained in Example 10 (88% NCL-6-I* 12% CL-19-I* | 122.5 |
| Product mixture obtained in Example 11 (84% NCL-6-I* 16% CL-19-I* | 120.4 |
| Product mixture obtained in Example 12 (86% NCL-6-I* 14% CL-19-I* | 119.7 |
| Mixture obtained by the method of Counsell, Example 13 (11% NCL-6-I* 89% CL-19-I* | 24.3 |
| CL-19-I* | 10.2 |

It is clear from the above results that NCL-6-I* and mixtures containing a large amount of this compound which are obtained by the method of this present invention show significant accumulation in the suprarenal and exhibit a markedly superior effect to those obtained by the conventional methods.

What is claimed is:

1. A compound represented by the following formula

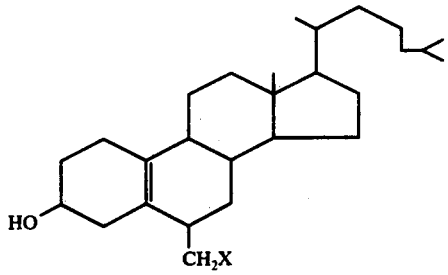

wherein X is iodine or radioactive iodine, said compound being substantially free of 19-iodocholest-5-en-3β-ol and radioiodinated-19-iodocholest-5-en-3β-ol.

2. A compound according to claim 1 wherein X is $I^{131}$ or $I^{125}$.

3. A composition comprising (A) about 80 to 99% of a compound represented by the following formula

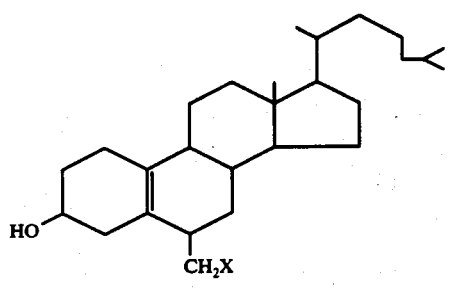

wherein X is radioactive iodine or iodine and (B) about 1 to 20% by weight, based on the total weight of the composition of 19-iodocholest-5-en-3β-ol, radioiodinated-19-iodocholest-5-en-3β-ol, or mixtures thereof.

4. A composition according to claim 3 wherein X is $I^{125}$ or $I^{131}$ and (B) is radioiodinated-19-iodocholest-5-en-3β-ol.

5. In a method for photoscanning the adrenal gland wherein a radioactive labelled compound is injected into a patient and thereafter a photoscan made of the patient's adrenal gland the improvement comprising using as the radioactive compound a compound of claim 1 wherein X is radioactive iodine.

6. In a method for photoscanning the adrenal gland wherein a radioactive labelled compound is injected in a patient and thereafter a photoscan made of the patient's adrenal gland the improvement comprising using as the radioactive compound a compound of claim 2 wherein X is radioactive iodine.

7. In a method for photoscanning the adrenal gland wherein a radioactive labelled composition is injected in a patient and thereafter a photoscan made of the patient's adrenal gland the improvement comprising using as the radioactive composition a composition of claim 3 wherein X is radioactive iodine and (B) is ratioiodinated-19-iodocholest-5-en-3β-ol.

8. A method for preparing a compound of claim 1 which comprises a. heating for a sufficient time in the range of from about 2 to about 8 hours and at a sufficient temperature to rearrange the substituent in the 19-position to the 6-position, a composition comprising
   1. a compound represented by the formula

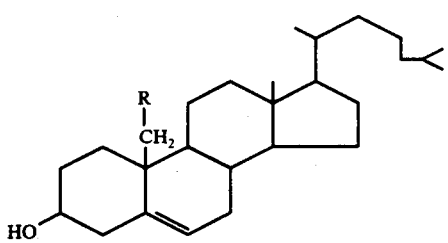

wherein R is a substituted sulfonyl group having the formula $R^1SO_2O$ wherein $R^1$ is an alkyl group, phenyl group or alkyl phenyl group wherein the alkyl portion contains 1 to 10 carbon atoms, a halogen atom, or radioactive iodine 2. a sufficient amount of iodine, radioactive iodine, alkali metal and ammonium salts thereof or mixtures thereof required to replace the substituent in the R position of said compound, said amount being about the stoichiometric amount required, and
   3. an inert polar organic solvent;

provided, however, when R is iodine said composition comprises (1) said compound, (2) radioactive iodine alkali metal radioactive iodides, or ammonium radioactive iodides, and (3) said solvent or said composition comprises (1) said compound (2) and said solvent; and further provided when R is radioactive iodine said composition comprises (1) said compound and (2) said solvent.

b. separating the compound represented by formula I by chromatography.

9. In a method for photoscanning the adrenal glands wherein a radioactive labeled composition is injected in a patient and thereafter a photoscan made of the patient's adrenal glands, the improvement comprising using as the radioactive composition a composition of claim 3 wherein X is $I^{125}$ or $I^{131}$ and (b) is radioiodinated-19-iodocholest-5-en-3β-ol.

10. A compound of the formula:

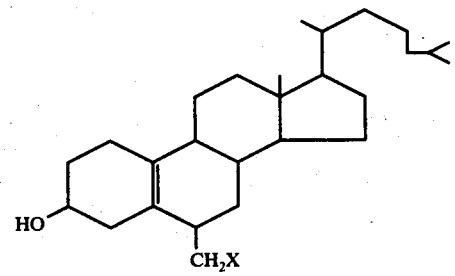

wherein X is selected from the group consisting of iodo and radio active iodine isotope derivative.

* * * * *